(12) United States Patent
Early

(10) Patent No.: US 11,851,394 B2
(45) Date of Patent: *Dec. 26, 2023

(54) PROCESS FOR SYNTHESISING METHANOL

(71) Applicant: JOHNSON MATTHEY DAVY TECHNOLOGIES LIMITED, London (GB)

(72) Inventor: Simon Robert Early, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 123 days.

This patent is subject to a terminal disclaimer.

(21) Appl. No.: 17/594,901

(22) PCT Filed: May 11, 2020

(86) PCT No.: PCT/GB2020/051141
§ 371 (c)(1),
(2) Date: Nov. 2, 2021

(87) PCT Pub. No.: WO2020/249923
PCT Pub. Date: Dec. 17, 2020

(65) Prior Publication Data
US 2022/0204429 A1 Jun. 30, 2022

(30) Foreign Application Priority Data
Jun. 12, 2019 (GB) ..................... 1908450

(51) Int. Cl.
*C07C 29/151* (2006.01)
(52) U.S. Cl.
CPC ................. *C07C 29/1518* (2013.01)

(58) Field of Classification Search
CPC ............... C07C 29/1518; C07C 31/04; C01B 2203/0233; C01B 2203/0244;
(Continued)

(56) References Cited

U.S. PATENT DOCUMENTS 4,321,234 A 3/1982 Ohsaki et al.
4,411,877 A 10/1983 Notman
(Continued)

FOREIGN PATENT DOCUMENTS

EP 1412312 A1 4/2004
EP 2228358 A1 9/2010
(Continued)

*Primary Examiner* — Jafar F Parsa
(74) *Attorney, Agent, or Firm* — BakerHostetler

(57) ABSTRACT

A process for synthesising methanol comprising the steps of (i) forming a synthesis gas containing hydrogen, carbon monoxide and carbon dioxide from a hydrocarbon feedstock in a reforming unit; (ii) cooling the synthesis gas in one or more stages of heat exchange, and recovering process condensate from the cooled synthesis gas; (iii) passing a feed gas comprising the make-up gas to a methanol synthesis loop comprising one or more methanol synthesis reactors; (iv) recovering a product gas mixture containing methanol from the methanol synthesis loop, cooling the product gas mixture to below the dew point to condense crude methanol, and separating the crude methanol from an unreacted gas mixture; and (v) recycling a portion of the unreacted gas mixture to the methanol synthesis loop and recovering a portion of the unreacted gas mixture as a purge gas stream.

15 Claims, 1 Drawing Sheet

(58) Field of Classification Search
CPC .... C01B 2203/0255; C01B 2203/0261; C01B 2203/062; C01B 2203/143
See application file for complete search history.

(56) References Cited

U.S. PATENT DOCUMENTS

| | | |
|---|---|---|
| 4,788,175 A | 11/1988 | Short et al. |
| 5,827,901 A | 10/1998 | Konig et al. |
| 6,191,174 B1 | 2/2001 | Early et al. |
| 6,218,439 B1 | 4/2001 | Kobayashi et al. |
| 7,790,775 B2 | 9/2010 | Early |
| 8,785,506 B2 | 7/2014 | Gamlin |
| 2008/0317646 A1 | 12/2008 | Morisaka et al. |
| 2009/0105356 A1 | 4/2009 | Bormann et al. |
| 2009/0184293 A1* | 7/2009 | Han ................ C01B 3/382 252/376 |
| 2011/0160313 A1 | 6/2011 | Ji |
| 2018/0305281 A1* | 10/2018 | Dahl ................ B01L 3/06 |

FOREIGN PATENT DOCUMENTS

| | | |
|---|---|---|
| WO | 2005/070855 A1 | 8/2005 |
| WO | 2006/126017 A1 | 11/2006 |
| WO | 2011088981 A1 | 7/2011 |
| WO | 2016/180812 A1 | 11/2016 |
| WO | 2017/121980 A1 | 7/2017 |
| WO | 2017/121981 A1 | 7/2017 |
| WO | 2019008315 A1 | 1/2019 |

* cited by examiner

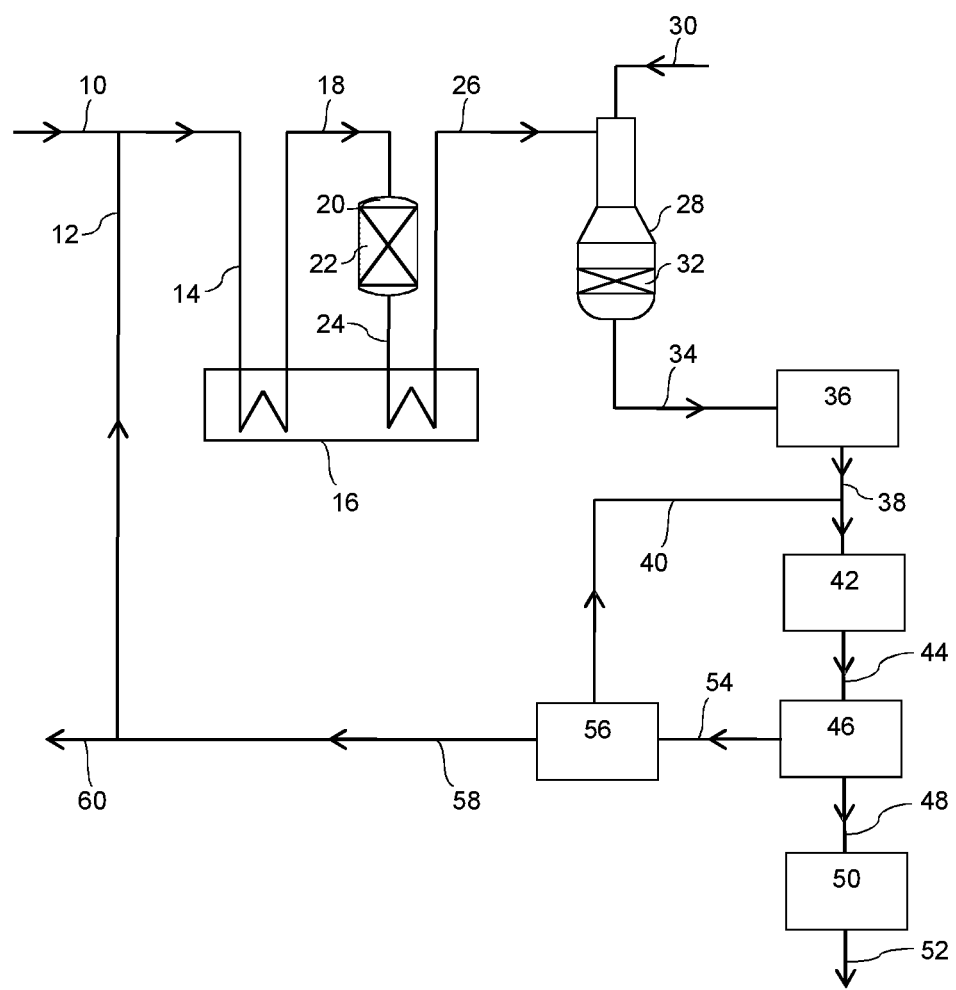

PROCESS FOR SYNTHESISING METHANOL

This invention relates to a process for synthesising methanol.

Methanol synthesis is generally performed by passing a synthesis gas comprising hydrogen and carbon monoxide and/or carbon dioxide at an elevated temperature and pressure through one or more beds of a methanol synthesis catalyst, which is often a copper-containing composition, in a synthesis reactor. A crude methanol is generally recovered by cooling the product gas stream to below the dew point and separating off the product as a liquid. The crude methanol is typically purified by distillation. The process is often operated in a loop: thus unreacted gas may be recycled to the synthesis reactor as part of the feed gas via a circulator. Fresh synthesis gas, termed make-up gas, is added to the recycled unreacted gas to form the feed gas stream. A purge stream is often taken from the circulating gas stream to avoid the build-up of inert gasses in the loop.

Methanol synthesis may be described by the following two equations:

$$3\,H_2 + CO_2 \rightleftharpoons CH_3OH + H_2O$$

$$2\,H_2 + CO \rightleftharpoons CH_3OH$$

There are two stoichiometric values that are commonly used to describe the proportions of the reactants fed to the methanol synthesis reactor. These are R and Z and may be determined from the molar concentrations of the components in the synthesis gas as follows;

$$R = ([H_2] - [CO_2])/([CO] + [CO_2])$$

$$Z = [H_2]/(2[CO] + 3[CO_2])$$

In addition, for methanol synthesis, it is often useful to determine a value S; being the sum of the $Nm^3/h$ of $H_2 + Nm^3/h$ of CO in the synthesis gas. S, Z and R may then be linked by the equation:

Maximum methanol make $(Nm^3/h) = Z.S/(R+1)$ for $Z \leq 1$

Maximum methanol make $(Nm^3/h) = S/(R+1)$ for $Z > 1$

The ideal stoichiometric mixture arises when there is enough hydrogen to convert all of the carbon oxides into methanol. This is when R=2 and Z=1. However different synthesis gas generation techniques produce different synthesis gases having different proportions of the reactants.

For example, U.S. Pat. No. 6,218,439 discloses a process for manufacturing methanol wherein a hydrocarbon-containing feedstock is subjected to steam reforming in a steam reformer heated by combustion and where carbon dioxide is recovered from the combustion gases and added to the feed to the steam reformer or the methanol synthesis. Purge gas recovered from the methanol synthesis is used as a fuel.

Using an autothermal reformer (ATR) generates a sub-stoichiometric synthesis gas. For typical operating conditions, the R-value of synthesis gas from an ATR is around 1.7 to 1.8 and this leads to flowsheets with lower conversion of feedstock to methanol compared to flowsheets with an R-value closer to 2. While R=2 is the theoretical ideal, practical issues, such as the quantity of carbon dioxide dissolved in the crude methanol and other liquid streams, mean that good overall flowsheet efficiency can be achieved with a R-value of 1.9 to 2.

Adjusting the operating conditions by reducing the steam to carbon ratio and increasing the feed gas temperature to the ATR increases the R-value but still does not achieve the desired stoichiometry of R=1.9 to 2. Furthermore, some changes, such as reducing the steam-to-carbon ratio, will increase the R-value but will also increase the methane slip from the ATR. This methane ends up as fuel, as methane is an inert in the methanol synthesis loop and so must be removed as part of the purge stream. With these "stretched" operating conditions there are remaining challenges to manage the R-value and the methane (fuel) balance.

To increase the R-value, it is possible to use a source of supplementary hydrogen. One source of supplementary hydrogen is to import gas rich in hydrogen from an external source. This may be possible in some circumstances, but few methanol plants are close to a suitable source of import gas rich in hydrogen. Another source of supplementary hydrogen is disclosed in WO2006/126017, whereby some of the reformed gas from the ATR is fed directly to a hydrogen recovery unit to supplement the hydrogen content of the methanol synthesis purge gas. This will increase the effective R-value, but it will further increase the surplus of fuel in the flowsheet where the common arrangement is for the off-gas from the hydrogen recovery to be used as fuel. With sufficient hydrogen available to add to the ATR feedstock, no pre-reforming may be necessary, but there may be problems of soot formation in the ATR if heavier feeds are used.

An alternative method to increase the R-value is to remove carbon dioxide from the synthesis gas feed to the loop, as is practiced on methanol plants that derive their synthesis gas from coal.

One way to reduce the methane slip, and so alleviate the surplus of fuel, is to reduce the operating pressure of the ATR. However, this requires greater compression power downstream when the reformed gas has to be compressed for the methanol synthesis loop.

A better solution is required that can provide both reformed gas with an optimised R-value for the synthesis of methanol and simultaneously avoid an excess of fuel.

The Applicant has found that suitable make-up gas for a methanol process may be generated by splitting the loop purge into a hydrogen-rich gas, which is returned to the loop, and a carbon-rich gas. The carbon-rich gas can be used as fuel, but the fuel value of the carbon-rich gas will often exceed the fuel requirements of fired heaters typically included in the flowsheet. The Applicant has found that a significant fraction of the carbon-rich gas can be recycled as feedstock to the ATR, such that the remaining carbon-rich gas is no longer in surplus compared to the fuel requirement of the fired heater. Carbon dioxide can optionally be removed from the carbon-rich gas flow, which will increase the R-value of the reformed gas at the exit of the ATR.

Accordingly the invention provides a process for synthesising methanol comprising the steps of (i) forming a synthesis gas containing hydrogen, carbon monoxide and carbon dioxide from a hydrocarbon feedstock in a reforming unit comprising an adiabatic pre-reformer and autothermal reformer in series; (ii) cooling the synthesis gas in one or more stages of heat exchange, and recovering process condensate from the cooled synthesis gas to form a make-up gas having a stoichiometry value, R, in the range 1.80 to 1.95; (iii) passing a feed gas comprising the make-up gas to a methanol synthesis loop comprising one or more methanol synthesis reactors; (iv) recovering a product gas mixture containing methanol from the methanol synthesis loop, cooling the product gas mixture to below the dew point to condense crude methanol, and separating the crude methanol from an unreacted gas mixture; and (v) recycling a portion of the unreacted gas mixture to the methanol synthesis loop and recovering a portion of the unreacted gas mixture as a purge gas stream, wherein a hydrogen-rich stream and a carbon-rich stream are separated from the purge gas stream, a portion of the hydrogen-rich stream is fed to the methanol synthesis loop and a portion of the carbon-rich stream is fed to the reforming unit.

By "carbon-rich stream" we mean a gas stream that has a higher proportion of carbon containing compounds (carbon monoxide, carbon dioxide and methane) than the purge gas. While individual components may have the same, or even lower, proportion than in the purge gas, the total of all carbon-containing components will be in a higher proportion in the carbon-rich gas compared to the purge gas.

In the present invention, the purge gas is split into a hydrogen-rich gas and a carbon-rich gas. Whereas it is possible to recycle only one of the streams and use the other as fuel, the Applicant has found that there is an improvement if both streams are recycled at least partially, as claimed. The hydrogen-rich stream is usefully recycled to the synthesis loop, where it is used to increase the R value of the gas at the inlet of the methanol synthesis reactor. The carbon-rich gas is partially recycled as feedstock with only a fraction required as fuel. In this way, the problem of having an excess of fuel gas is avoided.

In the process of the invention the hydrocarbon feedstock may be any gaseous or low boiling hydrocarbon feedstock such as natural gas, associated gas, LPG, petroleum distillate or naphtha.

It is preferably methane, associated gas or natural gas containing a substantial proportion, e.g. over 85% v/v methane. Natural gas is an especially preferred feedstock. The feedstock may be available at a suitable pressure or may be compressed to a suitable pressure, typically in the range 10-100 bar abs.

If the hydrocarbon feedstock contains sulphur compounds, before or after compression, the feedstock is preferably subjected to desulphurisation, e.g. hydrodesulphurisation using Co or Ni catalysts and absorption of hydrogen sulphide using a suitable absorbent, e.g. a zinc oxide bed. To facilitate this and/or reduce the risk of soot formation in the reforming process, hydrogen is preferably added to the hydrocarbon feedstock. The amount of hydrogen in the resulting mixed gas stream may be in the range 1-20% vol, but is preferably in the range 1-10%, more preferably in the range 1-5%. In a preferred embodiment a portion of the hydrogen-rich stream is mixed with the hydrocarbon feed stream. The hydrogen stream may be combined with the hydrocarbon upstream and/or downstream of any hydrodesulphurisation stage.

The hydrocarbon feedstock is subjected to steam reforming in the reforming unit. In steam reforming, the hydrocarbon feedstock is mixed with steam: this steam introduction may be effected by direct injection of steam and/or by saturation of the hydrocarbon feedstock by contact of the latter with a stream of heated water in a saturator. One or more saturators may be used. If desired, a portion of the hydrocarbon feedstock may bypass the steam addition, e.g. the saturator. The amount of steam introduced may be such as to give a steam to carbon ratio of 1 to 3, preferably 1 to 2, i.e. 1 to 2 moles of steam per gram atom of hydrocarbon carbon in the hydrocarbon feedstock. The amount of steam is preferably minimised as this leads to a lower cost, more efficient process. It is preferred that the steam to carbon ratio is ≤1.5:1.

The hydrocarbon/steam mixture is desirably pre-heated prior to reforming. This may be achieved by using a fired heater. The fired heater is suitably heated by combustion of a portion of the hydrocarbon, typically with waste fuel gases separated from downstream processing, which preferably includes a portion of the carbon-rich gas.

A carbon-rich stream is also fed to the reforming unit. This may be conveniently achieved by combining the hydrocarbon or hydrocarbon and steam mixture with the carbon rich stream using any known method.

The resultant hydrocarbon feedstock/steam/carbon-rich stream feed gas mixture is then subjected to reforming in a reforming unit in two stages in series: a first stage, which may be termed pre-reforming, and a second stage, which may be termed secondary or autothermal reforming. In the first stage, the feed gas mixture is subjected to a step of adiabatic steam reforming. In such a process, the feed gas mixture, is desirably heated to a temperature in the range 400-650° C., and then passed adiabatically through a bed of a suitable catalyst, usually a catalyst having a high nickel content, for example above 40% by weight. During such an adiabatic reforming step, any hydrocarbons in the feed gas mixture higher than methane react with steam to give a pre-reformed gas mixture comprising methane, steam carbon oxides and hydrogen. The use of such an adiabatic pre-reforming step is desirable to ensure that the feed to the autothermal reformer contains no hydrocarbons higher than methane and also contains a significant amount of hydrogen. This may be desirable in cases of low steam to carbon ratio mixtures in order to minimise the risk of soot formation in the autothermal reformer.

In the present invention the pre-reformed gas mixture, which comprises methane, hydrogen, steam and carbon oxides, is fed, preferably without adjustment of its composition, to an autothermal reformer in which it is subjected to autothermal reforming. Optionally, the carbon rich stream may be combined with the pre-reformed gas mixture fed to the autothermal reformer. If desired, the temperature and/or pressure of the pre-reformed gas mixture may be adjusted before feeding it to the autothermal reformer. The steam reforming reactions are endothermic and therefore, especially where natural gas is used as the hydrocarbon feedstock, it may be desirable to re-heat the pre-reformed gas mixture to the autothermal reformer inlet temperature. If the pre-reformed gas mixture is heated, this may conveniently also be performed in the fired heater used to pre-heat the feed to the pre-reformer.

The autothermal reformer will generally comprise a burner disposed near the top of the reformer, to which is fed the pre-reformed gas mixture and an oxygen-containing gas, a combustion zone beneath the burner through which, typically, a flame extends above a fixed bed of particulate steam reforming catalyst. In autothermal or secondary reforming, the heat for the endothermic steam reforming reactions is provided by combustion of hydrocarbon and hydrogen in the feed gas. The pre-reformed gas mixture is typically fed to the top of the reformer and the oxygen-containing gas fed to the burner, mixing and combustion occur downstream of the burner generating a heated gas mixture which is brought to equilibrium as it passes through the steam reforming catalyst. Whereas some steam may be added to the oxygen containing gas, preferably no steam is added so that the low overall steam ratio for the reforming process is achieved.

The autothermal reforming catalyst is usually nickel supported on a refractory support such as rings or pellets of calcium aluminate cement, alumina, titanium dioxide, zirconium dioxide and the like. In a preferred embodiment, the secondary reforming catalyst comprises a layer of a higher activity Ni and/or Rh on zirconium dioxide catalyst over a conventional Ni on alumina catalyst to reduce catalyst support volatilisation.

The oxygen-containing gas preferably comprises ≥95% vol. $O_2$, which may be provided by an air separation unit (ASU) or from another oxygen source.

The amount of oxygen-containing gas required in the autothermal reformer is determined by the desired composition of the product gas. In general, increasing the amount of oxygen, thereby increasing the temperature of the reformed gas leaving the autothermal reformer, causes the [Hz]/[CO] ratio to decrease and the proportion of carbon dioxide to decrease.

The amount of oxygen-containing gas added is preferably such that 40 to 60 moles of oxygen are added per 100 gram atoms of carbon contained in the feed to pre-reforming and autothermal reforming stages. Preferably the amount of oxygen added is such that the autothermally reformed gas leaves the autothermal reforming catalyst at a temperature in the range 750-1050° C. For a given feedstock/steam mixture, amount and composition of the oxygen-containing gas and reforming pressure, this temperature largely determines the composition of the autothermally-reformed gas.

The autothermally-reformed gas recovered from the autothermal reformer is a synthesis gas comprising hydrogen, carbon monoxide, carbon dioxide, methane and steam. The amount of methane is influenced by the ATR exit temperature. High exit temperatures lower the methane content of the reformed gas but also reduce the R-value.

After leaving the autothermal reformer, the autothermally-reformed gas is then cooled in one or more steps of heat exchange, generally including at least a first stage of steam raising. Preferably, following such steam raising the reformed gas is cooled by heat exchange with one or more of the following streams; the hydrocarbon feedstock, water (including process condensate), used to generate steam, which may be used for heating or used in the pre-reforming stage, the mixture hydrocarbon and steam, the pre-reformed gas mixture, and in the distillation of crude methanol For safety reasons the reformed gas is preferably not used to heat the oxygen-containing gas fed to the autothermal reformer.

The cooling is performed to lower the temperature of the synthesis gas from the autothermal reformer to below the dew point such that steam present in the synthesis gas condenses. The liquid process condensate may be separated from the synthesis gas, which may be termed make-up gas at this point, by conventional gas-liquid separation equipment.

The make-up gas comprises hydrogen, carbon monoxide, carbon dioxide, and small amounts of unreacted methane, argon and nitrogen. The R value of the make-up gas (before hydrogen-rich gas is added) is in the range 1.80 to 1.95. The R value is preferably at least 1.9, so that, once hydrogen recovery from the purge gas is included, the inlet of the converter has R≥3, preferably R≥4 and most preferably R≥5.

The make-up gas may be compressed in a synthesis gas compressor to the desired methanol synthesis pressure. A portion of the hydrogen-rich stream is fed to the methanol synthesis loop. This may be conveniently be achieved by mixing the compressed make-up gas with the hydrogen-rich stream before feeding the compressed make-up gas, mixed with the hydrogen rich gas, to the methanol synthesis loop.

Any methanol synthesis loop may be used in the process of the present invention. The methanol synthesis loop comprises one or more methanol synthesis reactors, for example first, second and optionally third methanol synthesis reactors, each containing a bed of methanol synthesis catalyst, arranged in series and/or parallel that each produce product gas streams containing methanol. The methanol synthesis loop may therefore comprise one, two or more methanol synthesis reactors each containing a bed of methanol synthesis catalyst, and each fed with a feed gas comprising hydrogen and carbon dioxide, each producing a gas mixture containing methanol. A product gas mixture containing methanol is recovered from at least one methanol synthesis reactor. Methanol is recovered from one or more of the product gas mixtures. This may be achieved by cooling one or more of the methanol product gas streams to below the dew point, condensing methanol, and separating a crude liquid methanol product from the unreacted gases.

Conventional heat exchange and gas-liquid separation equipment may be used. A particularly suitable heat exchange apparatus includes a gas-gas interchanger that uses a feed gas mixture for a methanol synthesis reactor to cool a methanol product gas stream from that reactor. The methanol product gas streams may be treated separately or may be combined before cooling and/or separating the crude liquid methanol product.

Separation of the crude liquid methanol product from one or more of the methanol product gas streams produces an unreacted gas mixture. A portion of the unreacted gas mixture is returned as a recycle or loop gas stream to one or more of the methanol synthesis reactors. Unreacted gas separated from a product gas mixture recovered from one methanol synthesis reactor may be returned to the same or a different methanol synthesis reactor. The unreacted gas mixture comprises hydrogen, carbon monoxide, and carbon dioxide and so may be used to generate additional methanol. The recycle gas stream may be recovered from at least one of one of the methanol product gas streams and recycled to at least one of the methanol synthesis reactors. If there is more than one recycle gas stream, these may be recycled separately to one or more of the methanol synthesis reactors or combined and fed to one or more of the methanol synthesis reactors.

The methanol synthesis reactor in the methanol synthesis loop may be an un-cooled adiabatic reactor. Alternatively, the methanol synthesis reactor may be cooled by heat exchange with a synthesis gas, such as in a quench reactor, or a reactor selected from a tube-cooled converter or a gas-cooled converter. Alternatively, the methanol synthesis reactor may be cooled by boiling water under pressure, such as in an axial-flow steam-raising converter, or a radial-flow steam-raising converter.

In an adiabatic reactor, the synthesis gas may pass axially, radially or axially and radially through a fixed bed of particulate methanol synthesis catalyst. The exothermic methanol synthesis reactions occur resulting in an increase in the temperature of the reacting gases. The inlet temperature to the bed therefore is desirably cooler than in cooled reactor systems to avoid over-heating of the catalyst which can be detrimental to selectivity and catalyst life. Alternatively, a cooled reactor may be used in which heat exchange with a coolant within the reactor may be used to minimise or control the temperature rise. A number of cooled reactor types exist that may be used. In one configuration, a fixed bed of particulate catalyst is cooled by tubes or plates through which a coolant heat exchange medium passes. In another configuration, the catalyst is disposed in tubes around which the coolant heat exchange medium passes. The methanol synthesis reactors may be cooled by the feed gas or by boiling water, typically under pressure. For example, the methanol synthesis reactor may be an axial steam raising converter, a radial-flow steam raising converter, a gas-cooled converter or a tube cooled converter.

In an axial-flow, steam-raising converter (aSRC), the synthesis gas typically passes axially through vertical, catalyst-containing tubes that are cooled in heat exchange with boiling water under pressure flowing outside the tubes. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in U.S. Pat. No. 8,785,506. Steam raising converters in which the catalyst is present in tubes cooled by boiling water under pressure offer a particularly useful means to remove heat from the catalyst.

In a radial-flow steam raising converter (rSRC) the synthesis gas typically passes radially (inwards or outwards) through a bed of particulate catalyst which is cooled by a plurality of tubes or plates through which boiling water under pressure is fed as coolant. Such reactors are known and are described for example in U.S. Pat. No. 4,321,234. They offer a lower pressure drop than an aSRC but have a more complicated internal construction.

In a tube-cooled converter, the catalyst bed is cooled by synthesis gas passing through tubes disposed within the bed that are open-ended and discharge the heated gas to the space above the catalyst within the reactor shell. The heated gas may then pass directly through the bed of catalyst without leaving the converter. TCC's can provide sufficient cooling area for a range of synthesis gas compositions and may be used under a wide range of conditions. As an alternative to a TCC, a gas-cooled converter (GCC) may be used to cool the catalyst bed by passing the synthesis gas though tubes or plates in a heat exchanger-type arrangement. In this case the heated synthesis gas is withdrawn from the converter before being returned back to the catalyst bed. An example of a GCC is described in U.S. Pat. No. 5,827,901.

Alternatively, the methanol synthesis reactor may be a quench reactor in which one or more fixed beds of particulate methanol synthesis catalyst are cooled by a synthesis gas mixture injected into the reactor within or between the beds. Such reactors are described, for example, in U.S. Pat. No. 4,411,877.

In a process comprising first and second methanol synthesis reactors, the first methanol synthesis reactor is preferably cooled by boiling water, such as in an axial-flow steam-raising converter or a radial-flow steam-raising converter, more preferably an axial-flow steam raising converter. The second methanol synthesis reactor may be a radial-flow steam-raising converter. Such arrangements are particularly useful in the present invention due to the characteristics and performance of these reactors with different feed gas mixtures. Alternatively, the second methanol may be cooled by a synthesis gas, e.g. a gas comprising hydrogen and carbon dioxide. Accordingly, the second methanol synthesis reactor may be a cooled reactor selected from a tube cooled converter (TCC) and a gas-cooled converter (GCC). A tube-cooled converter is preferred because of its simpler design. If a third methanol synthesis reactor is present, it is preferably cooled by boiling water. The third methanol synthesis reactor may then suitably be a steam-raising converter selected from an axial-flow steam-raising converter and a radial-flow steam-raising converter, most preferably an axial-flow steam raising converter. The first and second methanol synthesis reactors may be connected in series in which case the synthesis gas fed to the second methanol synthesis reactor comprises at least a portion of a methanol product gas stream recovered from the first methanol synthesis reactor. In such an arrangement, preferably the synthesis gas fed to the second methanol synthesis reactor comprises all of the methanol product gas stream recovered from the first methanol synthesis reactor. Particularly preferred methanol loops are described in U.S. Pat. No. 7,790,775, WO2017/121980 and WO2017/121981.

The methanol synthesis catalysts in each of the methanol synthesis reactors may be the same or different. The methanol synthesis catalysts are preferably copper-containing methanol synthesis catalysts, which are commercially available. In particular, the methanol synthesis catalysts are one or more particulate copper/zinc oxide/alumina catalysts, which may comprise one or more promoters. Particularly suitable catalysts are Mg-promoted copper/zinc oxide/alumina catalysts as described in U.S. Pat. No. 4,788,175.

Methanol synthesis may be effected in the one or more methanol synthesis reactors at pressures in the range 10 to 120 bar abs, and temperatures in the range 130° C. to 350° C. The pressures at the one or more reactor inlets is preferably 50-100 bar abs, more preferably 70-90 bar abs. The temperature of the synthesis gas at the one or more reactor inlets is preferably in the range 200-250° C. and at the one or more reactor outlets preferably in the range 230-280° C.

The portion of the unreacted gas mixture making up the recycle gas stream to the methanol synthesis loop will typically be at a lower pressure than the make-up gas and so preferably the recycle gas stream is compressed by one or more compressors or circulators. At least one compressor is used to circulate the unreacted gas stream. The resulting compressed recycle gas stream may be mixed with make-up gas and the hydrogen-rich stream to form the feed to the one or more methanol synthesis reactors in the methanol synthesis loop.

The recycle ratios to form the feed gas mixtures to the one or more methanol synthesis reactors may be in the range 0.5:1 to 5:1 preferably 1:1 to 3:1. By the term "recycle ratio", we mean the molar flow ratio of the recycled unreacted gas stream to the make-up gas that form the gas mixtures fed to the one or more methanol synthesis reactors.

It will be understood that by adding the hydrogen-rich gas stream to the make-up gas, that the stoichiometry value R will be increased. Preferably the R value is increased to a value greater than 1.95 and more preferably to a value in the range of 1.95 to 2.45, or higher.

A portion of the unreacted gas mixture separated from the crude liquid methanol is removed from the loop as the purge gas stream. The purge gas stream may be removed continuously or periodically to prevent the unwanted build-up of inert gases, such as nitrogen, argon and methane in the synthesis loop. The purge gas stream may be recovered from the separated unreacted gases before or after compression in the circulator. Purge gas streams, especially in processes using steam reforming as a source of the make-up gas, are hydrogen rich. The purge stream preferably contains 50-90% by volume of hydrogen and one or more of carbon monoxide, carbon dioxide, nitrogen, argon and methane.

In the present invention, at least a portion of the purge gas stream is separated into a hydrogen-rich gas stream and a carbon-rich gas stream. Preferably all of the purge gas stream is subjected to the separation step. A portion of the hydrogen-rich stream is fed to the methanol synthesis loop and a portion of the carbon-rich stream is fed to the reforming unit. The separation of the hydrogen-rich and carbon-rich gas streams may be practiced using known separation equipment such as hydrogen membrane separator or a pressure swing adsorption unit, a cold box separation system or any combination of these. Using these techniques over 50% of the hydrogen present in the purge gas stream may be recovered.

Where a membrane is used to separate the hydrogen-rich stream, the carbon-rich stream will be at a pressure that enables it to be sent for use as part of the hydrocarbon feedstock for reforming without further compression. This is highly desirable. Furthermore, modern membranes offer a way to split nitrogen from methane, so using an appropriate membrane material, or a two-stage separation using two membranes, offers the possibility of producing three streams, namely:

(1) a hydrogen-rich stream recycled to the methanol loop;
(2) a methane-rich stream recycled as the portion of the carbon-rich stream to the reformer unit; and
(3) a stream with a relatively high nitrogen:methane ratio to send to a fired heater as fuel.

Where a pressure swing absorption system is used to separate the hydrogen-rich stream, the carbon-rich stream will be at a low pressure, typically 2-5 bar abs, and so is less preferred in the present invention.

The hydrogen-rich gas stream recovered from the purge gas stream desirably comprises >95% by volume of $H_2$. The separated hydrogen, in addition to being recycled to the methanol loop may also be used upstream in hydrodesulphurisation of the hydrocarbon feedstock and/or used to strip dissolved gases from the crude methanol. However, in a preferred embodiment, at least 90% by volume of the separated hydrogen-rich gas stream is fed to the methanol synthesis loop.

A portion of the carbon-rich gas stream, which will typically contain carbon oxides and methane, is fed to the synthesis gas generation step in the reforming unit to form part of the make-up gas. However, preferably a portion of the carbon-rich gas is burned as fuel, e.g. in a fired heater, to control the build-up of inert gases such as nitrogen from the hydrocarbon and argon from the oxygen gas stream.

Operating a methanol synthesis reactor at a low exit temperature increases the $CO_2/CO$ ratio in the unreacted gas and so can change in the quantity of $CO_2$ dissolved in the crude methanol and leaving in the purge gas stream. If the purge gas stream is fed to a separation unit designed to maximise the rejection of $CO_2$ to fuel, then this removes the need for a $CO_2$ removal system. However, if the R-value of the make-up gas is less than 1.80, or if the $CO_2$ removed in the crude methanol and removed via the fuel is not sufficient, then a $CO_2$ removal unit may be included to provide the desired R-value in the enriched gas fed to the methanol synthesis unit. Therefore, in some embodiments, the carbon-rich stream may be subjected to a further separation to remove carbon dioxide and form a methane-rich stream that is returned as the portion of the carbon-rich stream to the reformer unit. The separation unit in this case may be a $CO_2$ removal unit. The $CO_2$ removal unit may be any conventional $CO_2$ removal unit that operates by physical absorption, chemical absorption, adsorption into a porous material, or uses a membrane to selectively separate $CO_2$ from the carbon-rich stream, thereby forming a methane-rich stream. A membrane $CO_2$-removal unit is preferred as it may be conveniently combined with a membrane separation unit used to provide the hydrogen-rich stream. The recovered $CO_2$ stream may contain small amounts of methane and inerts and so may be used as a fuel, e.g. in a fired heater.

The purge gas stream mixture may contain methanol and so, if desired, upstream of the separation of the hydrogen-rich gas and the carbon-rich gas, methanol may be recovered from the purge gas stream using a water wash, and the recovered methanol and water sent for purification with the crude methanol.

The crude methanol stream recovered from the methanol production unit contains water, along with small amounts of higher alcohols and other impurities. The crude methanol may first be fed to a flash column where dissolved gases are released and separated from the crude liquid methanol stream. The crude liquid methanol may also be subjected to one or more purification stages including one or more, preferably two or three, stages of distillation in a methanol purification unit comprising one, two or more distillation columns. The de-gassing stage and distillation stages may be heated using heat recovered from the process, for example in the cooling of a product gas stream, or by other sources. Preferably at least a portion of the crude methanol is purified by distillation to produce a purified methanol product.

The purified methanol product may be subjected to further processing, for example to produce derivatives such as dimethyl ether or formaldehyde. Alternatively, the methanol may be used as a fuel.

The invention will be further described by reference to the figures in which;

FIG. 1 depicts a process according to one embodiment of the invention.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

In FIG. 1, a mixture of natural gas and steam supplied by line 10 is mixed with a carbon-rich stream 12 and the resulting mixture fed via line 14 to a fired heater 16 where it is heated. The heated gas mixture is fed from the fired heater 16 by line 18 to a pre-reformer 18 containing a fixed bed of particulate steam reforming catalyst 20. The heated gas mixture is reformed adiabatically over the catalyst thereby converting higher hydrocarbons present in the natural gas to methane The pre-reformed gas mixture is fed from the pre-reformer 20 by line 24 to the fired heater 16 where it is heated to the autothermal reformer inlet temperature. The re-heated pre-reformed gas mixture is fed from the fired heater 16 via line 26 to an autothermal reformer 28 fed with an oxygen stream 30. In the autothermal reformer, the pre-reformed gas mixture is partially combusted with the oxygen in a burner mounted near the top and the resulting hot, partially-combusted gas brought to equilibrium through a bed of steam reforming catalyst 32 disposed beneath the burner. The resulting autothermally reformed synthesis gas stream is fed from the autothermal reformer 28 via line 34 to a heat recovery unit 36 comprising one or more heat exchangers, where it is further cooled to below the dew point to condense steam. Process condensate is removed from the cooled gas mixture using gas-liquid separation equipment in the heat recovery unit to produce a make-up gas. The make-up gas is recovered from the heat recovery unit 36 via line 38, combined with a hydrogen-rich gas stream fed via line 40, compressed in a synthesis gas compressor 42 and fed from the compressor 42 via line 44 to a methanol synthesis unit 46.

The methanol synthesis unit comprises a methanol synthesis loop in which the compressed mixture of make-up gas and hydrogen-rich gas is mixed with a recycled stream of unreacted gas comprising hydrogen, carbon dioxide and carbon monoxide, and fed to one, two or more methanol synthesis reactors, each containing a methanol synthesis catalyst, operating in series or parallel to generate a product gas stream containing methanol. The product gas stream is cooled to condense and separate a liquid crude methanol from unreacted gas, a portion of which is compressed in a circulator and recycled to the first, second or further methanol synthesis reactor. The crude liquid methanol is recovered from the methanol synthesis unit 46 and fed via line 48 to a methanol purification unit 50 where it is subjected to de-gassing and one, two or three stages of distillation to produce a purified methanol product recovered from the purification unit 50 via line 52.

A portion of the unreacted gas is withdrawn from the methanol synthesis unit 46 upstream of the circulator and passed as a purge gas stream from the methanol synthesis unit 46 via line 54 to a hydrogen separation unit 56 in which the purge gas stream is separated into a hydrogen-rich stream and a carbon-rich stream by passing the purge gas stream through a membrane. The carbon-rich stream is recovered from the separation unit 56 by line 58, a portion withdrawn from line 58 via line 60 for use as a fuel gas, e.g. in the fired heater 16, and the remaining portion fed via line 12 to the hydrocarbon and steam feed line 10. The hydrogen-rich gas stream is recovered from the separation unit 56 via line 40 and mixed with the make-up gas in line 38 to form an enriched feed gas. The enriched feed gas is preferably fed to a suction or interstage of the synthesis gas compressor 42 to form a compressed enriched feed gas for the methanol synthesis unit 46.

In an alternative arrangement, the carbon-rich stream in line 58 is subjected to further separation in a further separation unit (not shown) that removes at least a portion of the carbon dioxide from the carbon-rich stream, thereby generating a methane-rich stream and the methane rich stream is fed to the reformer unit as the carbon-rich stream. Inert gases are separated with the removed carbon dioxide and the inerts and removed carbon dioxide used as a fuel, e.g. in the fired heater 16.

The invention will be further described by reference to the following calculated examples prepared using conventional modelling software suitable for methanol processes. These examples all produce the same quantity of $H_2+CO$ in $Nm^3/h$ at the exit of the ATR and are therefore capable of producing the same amount of product methanol.

EXAMPLE 1

Example 1 is an example of a flowsheet in accordance with FIG. 1. The carbon-rich gas in the example is the retentate from a membrane separation unit that is fed with the purge gas from the methanol synthesis loop. 95% of the carbon-rich gas retentate is recycled as feedstock and added downstream of the pre-reformer. The remaining 5% of the retentate is used as fuel for the fired heater, supplemented with natural gas.

EXAMPLE 2

Example 2 is the same as Example 1, but the CO2 has been removed from the retentate recycle to demonstrate the impact of CO2 removal. The oxygen flow has been kept the same as Example 1.

COMPARATIVE EXAMPLE 3

Example 3 is a comparative example where none of the carbon-rich gas is recycled to the ATR as feedstock. The oxygen flow has been kept the same as Example 1.

COMPARATIVE EXAMPLE 4

Example 4 is a comparative example where none of the carbon-rich gas is recycled to the ATR as feedstock. The oxygen flow has been increased so that the ATR exit temperature is the same as Example 1.

The results are set out in the following Table.

| | Example 1 | Example 2 | Comparative Example 3 | Comparative Example 4 |
|---|---|---|---|---|
| Recycle of carbon-rich gas | Yes | Yes | No | No |
| $CO_2$ removal from carbon-rich recycle | No | Yes | — | — |
| Natural gas flow relative to Example 1 | 100% | 100% | 112% | 110% |
| Oxygen flow to ATR relative to Example 1 | 100% | 100% | 100% | 101% |
| Temperature at exit of ATR | 970° C. | 973° C. | 955° C. | 970° C. |
| R-value of reformed gas at exit of ATR | 1.906 | 1.946 | 1.945 | 1.936 |

The results illustrate an enhanced efficiency compared to the comparative examples. The decision to remove $CO_2$ from the carbon-rich recycle will depend on the design of the methanol loop, and the effect of an R-value less than 2.

The invention claimed is:

1. A process for synthesising methanol comprising the steps of (i) forming a synthesis gas containing hydrogen, carbon monoxide and carbon dioxide from a hydrocarbon feedstock in a reforming unit comprising an adiabatic pre-reformer and autothermal reformer in series; (ii) cooling the synthesis gas in one or more stages of heat exchange, and recovering process condensate from the cooled synthesis gas to form a make-up gas having a stoichiometry value, R, in the range 1.80 to 1.95; (iii) passing a feed gas comprising the make-up gas to a methanol synthesis loop comprising one or more methanol synthesis reactors; (iv) recovering a product gas mixture containing methanol from the methanol synthesis loop, cooling the product gas mixture to below the dew point to condense crude methanol, and separating the crude methanol from an unreacted gas mixture; and (v) recycling a portion of the unreacted gas mixture to the methanol synthesis loop and recovering a portion of the unreacted gas mixture as a purge gas stream, wherein a hydrogen-rich stream and a carbon-rich stream are separated from the purge gas stream, a portion of the hydrogen-rich stream is fed to the methanol synthesis loop and a portion of the carbon-rich stream is fed to the reforming unit.

2. The process according to claim 1 wherein the hydrocarbon feedstock is natural gas.

3. The process according to claim 2 wherein the steam for reforming the natural gas is provided using a saturator.

4. The process according to claim 1 wherein the hydrocarbon is reformed in the adiabatic pre-reformer with steam at a steam to carbon ratio of ≤1.5:1.

5. The process according to claim 1 wherein the autothermal reformer comprises a burner disposed near the top of the reformer to which a pre-reformed gas from the adiabatic pre-reformer and an oxygen-containing gas are fed, a combustion zone beneath the burner through which a flame extends, above a fixed bed of particulate steam reforming catalyst.

6. The process according to claim 5 wherein the oxygen-containing gas comprises ≥95% vol. $O_2$.

7. The process according to claim 1 wherein the R value of the make-up gas, before hydrogen-rich gas is added, is in the range 1.80 to 1.95, and after the hydrogen-rich gas is added, the R value is increased.

8. The process according to claim 1 wherein the methanol synthesis loop comprises one, two or more methanol synthesis reactors each containing a bed of methanol synthesis catalyst, wherein the product gas mixture is recovered from at least one methanol synthesis reactor.

9. The process according to claim 8 wherein an unreacted gas mixture separated from a product gas mixture recovered from one methanol synthesis reactor is returned to the same or a different methanol synthesis reactor.

10. The process according to claim 8 wherein the methanol synthesis reactors are cooled by a synthesis gas or by boiling water.

11. The process according to claim 8 wherein methanol synthesis is effected in the one or more methanol synthesis reactors at pressures in the range 10 to 120 bar abs, and at temperatures in the range 130° C. to 350° C.

12. A process according to claim 1 wherein the separation of the hydrogen-rich and carbon-rich streams is accomplished using a hydrogen membrane separator or a pressure swing adsorption unit, or a cold box separation system, or any combination of these.

13. The process according to claim 1 wherein the carbon-rich stream is subjected to a further separation stream to remove carbon dioxide and form a methane-rich stream that is returned as the portion of the carbon-rich stream to the reformer unit.

14. The process according to claim 12 wherein the separation of the hydrogen-rich stream is accomplished using a membrane separator.

15. The process according to claim 1 wherein the crude methanol is subjected to one or more steps of distillation to produce a purified methanol product.

* * * * *